United States Patent [19]
Tunney et al.

[11] 3,992,706
[45] Nov. 16, 1976

[54] LIQUID LEVEL MONITORING APPARATUS

[76] Inventors: Thomas P. Tunney, 589 Stanton Ave., Baldwin, N.Y. 11510; James W. Campbell, 151 Lincoln Ave., Rockville Center, N.Y. 11570

[22] Filed: Jan. 5, 1976

[21] Appl. No.: 646,851

Related U.S. Application Data

[63] Continuation-in-part of Ser. No. 535,108, Dec. 20, 1974, abandoned.

[52] U.S. Cl. .................. 340/239 R; 128/DIG. 13; 128/214 E; 200/61.4; 200/81 R; 200/153 T; 222/66; 222/95
[51] Int. Cl.² ........................................ G08B 21/00
[58] Field of Search .............. 340/239 R, 241, 242, 340/244 R, 265; 222/45, 66, 95, 103; 200/61.4, 61.42, 61.23, 81 R, 153 T; 128/DIG. 12, DIG. 13, 214 E, 214 F, 238, 276;

[56] References Cited
UNITED STATES PATENTS

| | | | |
|---|---|---|---|
| 1,219,723 | 3/1917 | Gracey et al. | 340/229 |
| 1,816,464 | 7/1931 | Biggert, Jr. | 340/265 |
| 3,151,616 | 9/1964 | Selfon | 128/DIG. 12 |
| 3,640,277 | 2/1972 | Adelberg | 128/DIG. 12 |
| 3,884,228 | 5/1975 | Hahn | 340/239 R X |

FOREIGN PATENTS OR APPLICATIONS

| | | | |
|---|---|---|---|
| 1,528,024 | 4/1968 | France | 128/DIG. 13 |

*Primary Examiner*—John W. Caldwell
*Assistant Examiner*—Daniel Myer

[57] ABSTRACT

Apparatus for monitoring the drop of the level of the liquid in a plastic bag that is used during the intravenous administration of a solution includes a housing in which switch means having an integral, spring actuated contact means is mounted with the switch means being electrically connected to alarm means for generating a signal when the condition of the switch means changes in response to the reduction of the contents of the bag to a predetermined volume. A first arm is pivotally mounted so that a portion of the first arm engages a first surface of the bag. First spring means are employed for normally biasing the first arm in a direction towards the first surface of the bag. A second arm includes a portion that is in opposition to the bag engaging portion of the first arm so that the bag may be positioned therebetween and compressed thereby. The second arm also includes means for actuating the switch means. There is also provided a third, angularly adjustable arm together with a second spring that extends between the third arm and the second arm. When the contents of the plastic bag is reduced to the predetermined volume after the initiation of the administration of the solution the total force that will be exerted on the bag is represented by the sum of the forces exerted by the spring that actuates the switch means contacts and the second spring means. The total force that is required to change the condition of the switch means can be varied by angularly displacing the second arm.

13 Claims, 5 Drawing Figures

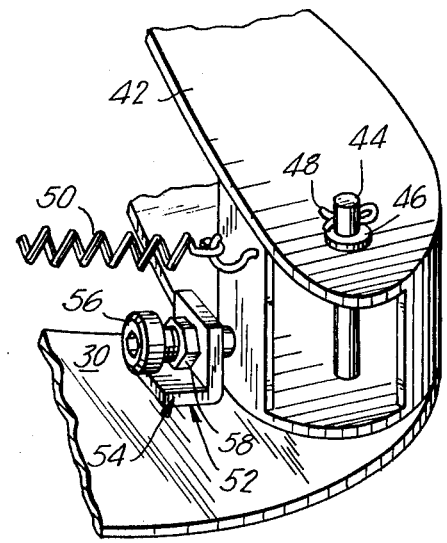
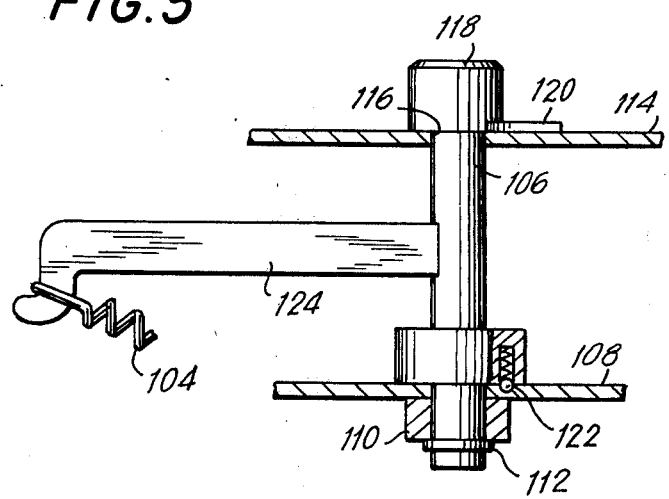
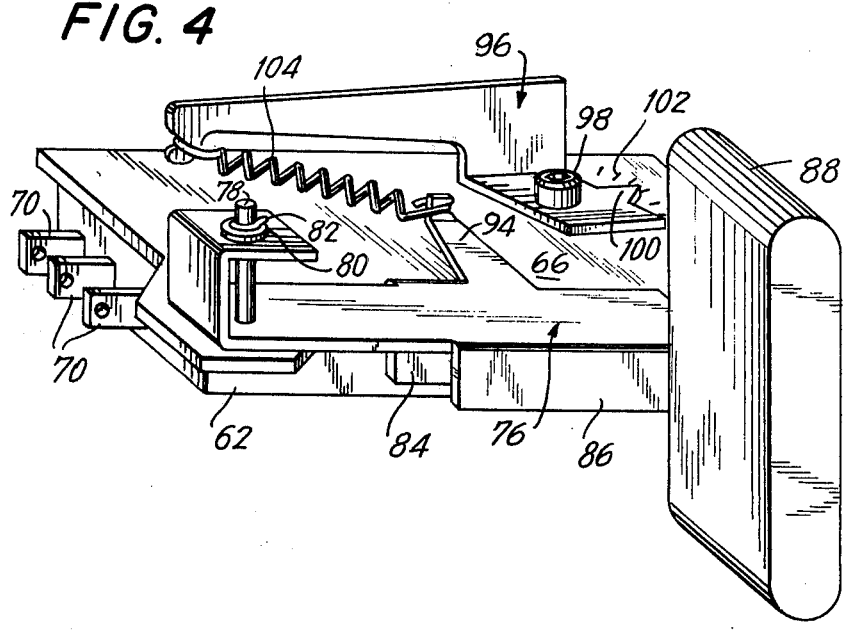

LIQUID LEVEL MONITORING APPARATUS

This application is a continuation-in-part of our copending application Ser. No. 535,108, filed Dec. 20, 1974, now abandoned.

The present invention relates generally to liquid level monitoring devices and more particularly to improved apparatus for indicating the reduction of fluid in an intravenous bag.

Present day medicine frequently requires some intravenous infusion during the stay of a patient in a hospital. However, if the apparatus associated with the intravenous infusion does not function properly or if there is some breakdown in the apparatus, the intravenous therapy may result in a substantial loss of valuable time for the hospital personnel as well as a definite hazard to the patient. Should the patient be adversely affected by a malfunction in the apparatus used for the intravenous infusion it is possible that either the hospital and its staff or the doctor, or both, will be subjected to a malpractice suit.

It is of the utmost importance in intravenous administration that, before the flow ceases and the bag empties, the medical personnel replace it with a fresh solution bag. If the solution does run dry before the medical personnel has either time to terminate the infusion or add a fresh bag of solution, there is a strong possibility that a clot will form that will plug the needle. This causes loss of staff time and adds material cost required in changing the intravenous set. The restart of the intravenous infusion is not only time consuming for medical personnel but, with a vein "cut-down", a physician must be called in.

Air and blood embolisms are significant hazards of infusion therapy and are associated with a delay in changing the solution bag. Failure to promptly change the solution bag allows the fluid level to drop in the tubing to approximately the level of the patient's chest. When this happens blood will be forced back into the needle causing a clot to form. Positive pressure applied in an attempt to flush the needle or lack of flow at the needle point within the vein favors platelet formation and clotting. Such a clot can prove fatal to the patient.

With proper notice to change the bag, the patient avoids discomfort and, in addition, preserves veins by avoiding the necessity of restarting the infusion with an attendant vein cut-down that requires the attendance of a physician. Additionally, many manpower hours during the course of the year will be saved if the apparatus used in the intravenous transfusion is reliable and if the medical personnel no longer require numerous trips to the patient's bedside to determine whether or not the bag should be changed.

The present invention overcomes many of the shortcomings in the prior art by providing novel means that permit accurate switch actuation in order to signal medical personnel that the solution bag requires changing. The requirement for changing the solution bag may occur either when the bag is empty or almost empty, or after a predetermined volume of the solution has been administered, depending upon the instructions given by the physician. The present invention provided a novel spring arrangement whereby at least a component of the force of a second spring is added to the spring force that actuates the contact means in a switch. By accurately controlling the magnitude of the component of the auxillary spring, the total force required to change the condition of the switch from either open to closed or from closed to open may be regulated. That is, depending upon the position of the structure that supports the auxillary spring, a component of the force exerted thereby can be either added to or substracted from the force exerted by the spring that actuates the contact means of the switch. It is the total force of the combined springs that determines the initiation of an alarm, either audible or visual, indicating that some attention must be given to the infusion set.

In one aspect of the present invention there is provided a housing having conventional switch means therein which have spring actuated contact means. The switch is adapted to be electrically connected to any suitable alarm for generating a signal when the condition of the switch means changes in response to the reduction of the contents of the infusion bag to a predetermined level. The bag is compressed on opposite sides thereof by first and second pivotally mounted arms with one of the arms being normally urged in a direction that would tend to press the bag while the second arm applies a restraining force to the bag in the opposite direction. A third arm provides support, in combination with the second arm, for a second or auxillary spring whose position may be adjusted by angularly displacing the third arm to thereby vary a component of the force of the auxillary spring. At a particular time during the intravenous infusion, the force applied by the first arm is terminated so that the total force being applied to the solution bag is represented by the combined forces of the spring that actuates the contact means of the switch and the active component force of the auxillary spring. The second or auxillary spring is arranged such that movement of the third arm in one angular direction will increase the total force acting on the solution bag while movement in the opposite angular direction will decrease the total force acting on the solution bag. The third arm that supports the auxillary spring may be adjusted either internally or externally of the apparatus.

Accordingly, it is an object of the present invention to provide an improved apparatus for monitoring the liquid level in the solution bag of an intravenous set.

Another object of the present invention, as described above, is to provide improved apparatus for generating a signal when the liquid in the solution bag of an intravenous set reaches a predetermined level.

A further object of the present invention is to provide an improved spring arrangement whereby the force required to change the condition of a switch used in an intravenous set for signaling the attainment of a predetermined level in the solution bag may be closely regulated, adjusted and varied.

It is a further object of the present invention to provide improved apparatus, as described above, that is relatively low in cost and which may be simply operated without complex adjustment to the apparatus.

Still another object of the present invention is to provide improved apparatus, as described above, that may be simply adjusted either externally or internally.

These and other objects, features and advantages of the invention will, in part, be pointed out with particularity, and will, in part, become obvious from the following more detailed description of the invention, taken in conjunction with the accompanying drawing, which forms an integral part thereof.

In the various figures of the drawing, like reference characters designate like parts. In the drawing:

FIG. 3 is a fragmentary perspective view illustrating a portion of the structure shown in FIG. 2;

FIG. 4 is a perspective view illustrating still other structure shown in FIG. 2; and FIG. 5 is a fragmentary elevational view illustrating an alternative modification of the embodiment of the invention shown in FIG. 2.

Figure 1:
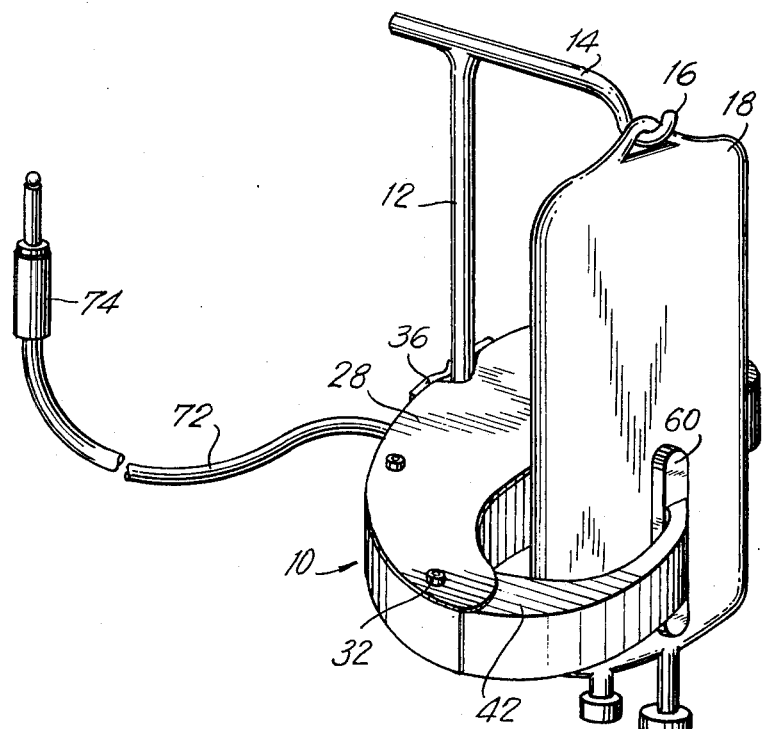
FIG. 1 is a perspective view illustrating one embodiment of the present invention as applied to an intravenous set utilizing a flexible, plastic bag.

Referring now to the drawing, and in particular to FIG. 1, there is shown the monitoring apparatus 10 comprising the present invention in use with an intravenous administration set that includes a conventional standard 12 having an arm 14 on the extremity of which a hook 16 is formed for receiving a flexible plastic bag 18 that contains the solution to be administered through a tube 20.

Figure 2:
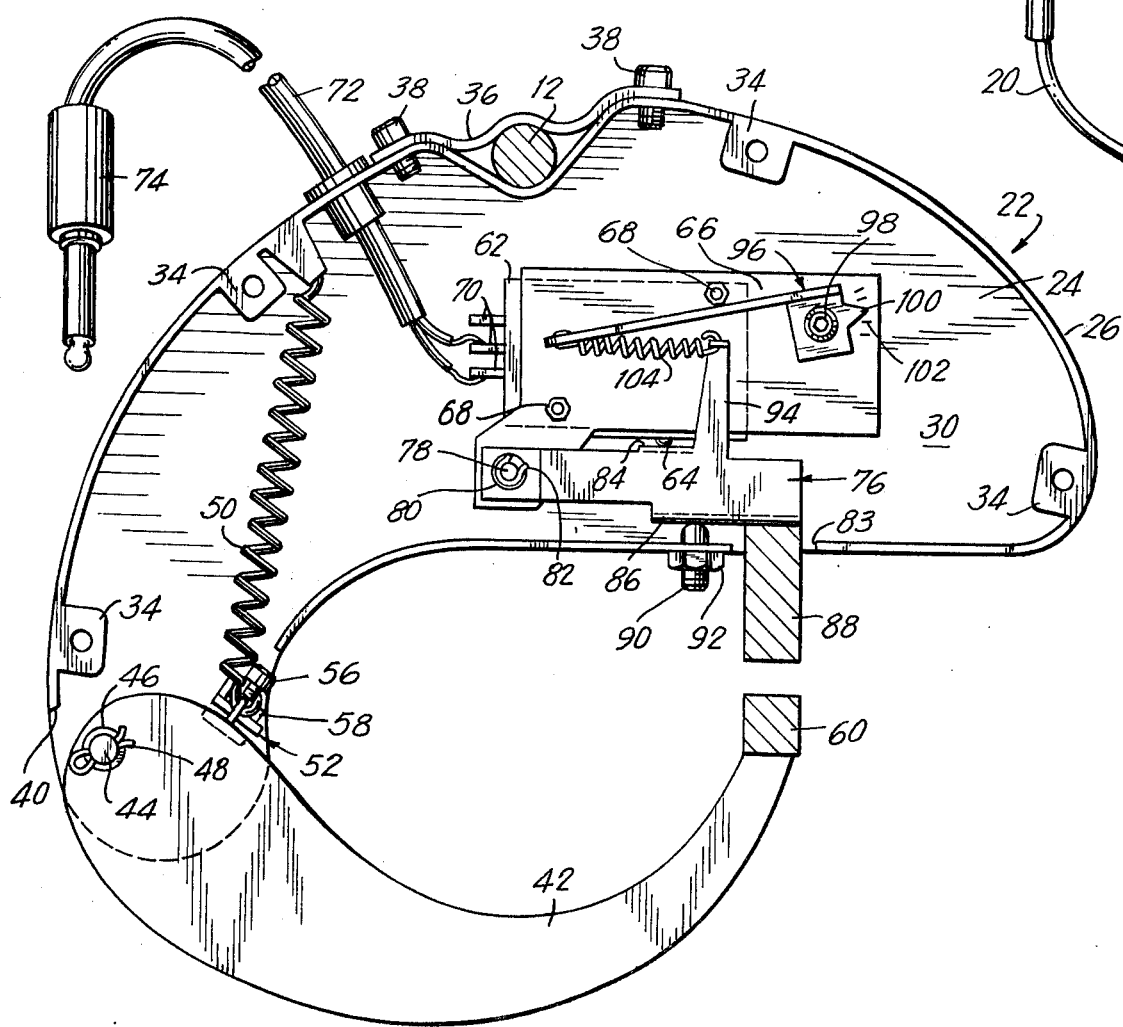
FIG. 2 is a plan view of the structure shown in FIG. 1 with the cover thereof removed and with portions thereof in section.

As shown best in FIG. 2, the monitoring apparatus 10 comprising the invention includes a housing generally designated by the reference character 22 having a base wall 24, a peripheral side wall 26 and a cover plate 28 (FIG. 1) which, in combination, define a chamber 30. The cover 28 may be secured in place by means of fasteners 32 which extend through the cover plate 28 and engage threaded tabs 34 which, by way of example, are integral with the peripheral side wall 26. It will be evident that other forms of construction could be employed for removably securing the cover 28. The housing 22 is removably and adjustably secured to the standard 12 by means of a clamp 36 and fasteners 38 that extend through the clamp 36 and which are threadably engaged in the peripheral side wall 26 of the housing 22. Once again, other forms of construction could be utilized for mounting the housing 22 on the standard 12.

Referring once again to FIG. 2 it will be seen that the housing 22 is provided with a first opening 40 for receiving one end of an arcuate first arm 42. A post or hinge pin 44 is mounted on the base wall 24 of the housing 22 in order to loosely support the first arm 42 which is captured by any suitable means such as a washer 46 and a cotter pin 48. For purposes to be described hereinafter, one end of an extension spring 50 is coupled (FIG. 3) to the first arm 42 proximate the rotational axis thereof and the other end of the spring 50 is coupled to a suitable portion of the sidewall 26 of the housing 22. Stop means generally designated by the reference character 52 limit the rotation of the first arm 42 in a counter clockwise direction as viewed in FIG. 2. The stop means 52, in the embodiment illustrated, is comprised of an L-shaped bracket 54 that is secured to the base wall 24 of the housing 26. A screw 56 is threaded into the upright leg of the bracket 54 and a stop nut 58 retains the screw 56 in the desired position so that the end thereof bears against a portion of the first arm 42. The end of the first arm 42 that is opposite the rotational axis thereof is provided with an elongated pad 60 that is adapted to engage one surface of the plastic bag 18.

A switch 62 having a spring actuated contact button 64 is mounted, together with a plate 66, on the base wall 24 of the housing 22 by means of screws 68. The switch 62 is provided with conventional terminals 70 to which conductor means 72 and a jack 74 may be connected so that the apparatus may be plugged into an existing nurse call system without any additional installation costs. However, the patient will still be able to activate the nurse call system while the bag is being monitored.

A second arm generally designated by the reference character 76 is pivotally mounted on the plate 66 by means of a hinge post 78, a washer 80 and a spring clip 82. The second arm 72 extends through a second opening 83 in the sidewall 26 of the housing 22 and is provided with a tab portion 84 that is arranged to engage and depress the push button 64 of the microswitch 62. A second tab 86 formed integrally with the second arm 76 is used to support a second bag engaging pad 88 that is in opposition to the bag engaging pad 60 so that the bag 18 may be positioned between the two pads 60 and 88 in order to be compressed thereby in a manner to be described more fully hereinafter. The second tab 86 is placed in opposition to stop means in the form of a screw 90 and a nut 92 that limits the angular movement of the second arm 76 in a clockwise direction as seen in FIG. 2.

A third arm, generally designated by the reference character 96 is also secured to the plate 66 by means of a screw 98. The third arm 96 is provided with an integral pointer 100 that overlays calibrations 102 formed on the top surface of the plate 66. One end of a second spring 104 is secured to the end of the third arm 96 that is opposite the pivot axis thereof defined by the screw 98. The other end of the spring 104 is secured to the extension 94 that is formed integrally with the second arm 76.

In operation, the bag 18 containing the solution that is to be intravenously administered is hung from the hook 16 of the standard 12. The first arm 42 is pulled outwardly, or in a clockwise direction as viewed in FIG. 2 so that the bag may be positioned between the two pads 60 and 88. Preferably, the bottom of the pads 60 and 88 are spaced upwardly from the bottom of the plastic bag 18 by approximately ⅜th inch. As the liquid is drained from the bag 18 during the intravenous infusion the bag 18 deflates and the spring 50 pulls the arm 42 and hence the pad 60 in a counter clockwise direction as viewed in FIG. 2. The opposite surface of the bag 18 is urged against the opposed pad 88. At a position determined by the setting of the screw 56 of the first stop means 52 the counter clockwise movement of the first arm 42 terminates. The clockwise force and movement of the second arm 76 as viewed in FIG. 2 is now opposed only by the lateral liquid forces within the bag 18 which liquid force is proportional to the height of the liquid level. The total force now exerted on the bag through the pad 88 is the sum total of the force exerted by the spring that actuates the switch 62 through the switch button 64 and the force of the second spring 104 that either adds to or substracts from the force of the switch contact spring. If the arm 96 is angularly displaced in a clockwise direction about the rotational axis defined by the screw 98 (FIG. 2) it tends to reduce the total force applied to the bag 18 by the pad 88. Conversely, if the third arm 96 is angularly displaced in a counter clockwise direction about the axis defined by the screw 98 as viewed in FIG. 2, it will increase the total force applied to the bag 18 by the pad 88. Thus, by varying the effective force of the second spring 104 the total force required to change the condition of the switch 62 may be varied. It should be noted that the switch 62 may be used to either open a circuit or close a circuit depending upon the requirement of the apparatus. In the example illustrated the nurse call alarm could be closed in order to generate either an audio and/or a visual alarm. It should be appreciated however that the switch 62 may also be used to open a circuit as in the shutting down of an electric pump or other equipment.

In the embodiment illustrated in FIGS. 2, 3 and 4, for example, the third arm 96 may be angularly displaced after the cover 28 is removed. In the embodiment illustrated in FIG. 5 a comparable adjustment may be made without removing the cover. In the FIG. 5 embodiment a shaft 106 is rotationally mounted on a plate 108 that corresponds in function and location to plate 66 in the first described embodiment. The shaft 106 may be captured by a washer 110 and a spring clip 112. The shaft 106 extends through a cover plate 114 having an opening 116 therein for that purpose. The shaft 106 terminates in a knob 118 that permits the angular displacement thereof and, in addition, the knob 118 may be provided with a pointer 120 that is in opposition to suitable calibrations formed on the top surface of the cover 114. If desired, a spring loaded detent mechanism generally designated by the reference character 122, may be provided so that angular displacement of the shaft 106 may take place in stepwise increments. Alternatively, any suitably means may be utilized for providing smooth or non-stepwise angular displacement of the shaft 106. A second spring 104 would be secured to a projection 124 that extends radially from the shaft 106 and would function in a manner described in connection with the previous embodiment.

Although not specifically illustrated it is also within the scope of the present invention to eliminate the first arm 42. The bag 18 would be hung such that the surface thereof that would normally be contacted by the pad 88 would be at a position approximately ⅝th inch behind the outermost face of the pad 88. Thus, the bag would be in a position off of a true vertical plane and would therefore impart a horizontal vector component force to the pad 88 that functions in the same manner as the pad 60. While this last alternative embodiment is somewhat easier to use in that the first arm 42 need not be manipulated, it does not have the same degree of accuracy as described in connection with the first embodiment.

There has been disclosed heretofore the best embodiment of the invention presently contemplated. However, it is to be understood that various changes and modifications may be made thereto without departing from the spirit of the invention.

What is claimed is:
1. Monitoring apparatus for use during the intravenous adminstration of a solution from a flexible plastic bag that is freely supported on an arm, said apparatus comprising:
   a. a housing;
   b. spring actuated switch means having integral contact means, said switch means being mounted on said housing and adapted to be electrically connected to alarm means for generating a signal when the condition of said switch means changes in responce to the reduction of the contents of the bag to a predetermined volume;
   c. a first arm pivotally mounted on said housing and having a portion thereof in engagement with said bag, said first arm including means for actuating said switch means;
   d. a second arm adjustably mounted on said housing; and
   e. first spring means extending between said first arm and said second arm whereby, when the contents of the plastic bag is reduced to said predetermined volume after the initiation of the administration of the solution contained therein, the total force exerted by the plastic bag overcomes the sum of the forces exerted by the spring that actuates said spring actuated switch means and said first spring means and wherein the force of said first spring means may be varied by displacing said second arm to thereby vary the total force required to change the condition of said switch means.

2. The monitoring apparatus according to claim 1 wherein there is further included a third arm having a bag engaging portion that is in opposition to the bag engaging portion of said first arm, means for mounting said third arm on said housing and means for urging the bag engaging portion of said third arm in a direction towards the bag engaging portion of said first arm.

3. The monitoring apparatus according to claim 2 wherein said third arm is angularly movable.

4. The monitoring apparatus according to claim 3 wherein there is further included stop means for limiting the angular movement of said third arm.

5. The monitoring apparatus according to claim 1 wherein calibration means are provided adjacent said second arm.

6. The monitoring apparatus according to claim 1 wherein said housing comprises a base wall, a peripheral sidewall and a cover and wherein said switch means, said second arm, said first spring means and at least a portion of said first and third arms are contained within said housing.

7. The monitoring apparatus according to claim 6 wherein there is an opening in said housing for receiving a portion of said first arm.

8. The monitoring apparatus according to claim 6 wherein there is an opening in said housing for receiving a portion of said third arm.

9. The monitoring apparatus according to claim 1 wherein said first spring means is arranged such that movement of said second arm in one direction will increase the sum of the spring forces and movement of said second arm in the opposite direction will decrease the sum of the spring forces.

10. The monitoring apparatus according to claim 1 further including means external of said housing and coupled to said second arm for displacing said second arm.

11. In monitoring apparatus for use during the intravenous administration of a solution from a plastic bag wherein the apparatus includes spring actuated switch means having integral contact means that are responsive to the movement of an arm that is displaced by the reduction of the volume of the contents of the bag in order to energize an alarm, the improvement comprising spring means adapted to be coupled to the arm that is responsive to the reduction in volume of the contents of the bag whereby the force exerted by said spring means, in combination with the force exerted by the spring actuating the spring actuated switch means represents the total force exerted on the bag at the time the alarm is energized.

12. The improvement according to claim 11 further including means for varying the force exerted by said spring means.

13. The improvement according to claim 12 wherein said force varying means is angularly adjustable.

* * * * *